United States Patent [19]
Heym et al.

[11] Patent Number: 5,633,131
[45] Date of Patent: May 27, 1997

[54] **RAPID DETECTION OF ISONIAZID RESISTANCE IN *MYCOBACTERIUM TUBERCULOSIS* PROBES FOR SELECTING NUCLEIC ACID ENCODING ISONIAZID RESISTANCE, AND METHODS AND KITS**

[75] Inventors: Beate Heym, Paris; Stewart T. Cole, Clamart, both of France; Douglas B. Young, Middlesex, United Kingdom; Ying Zhang, London, England

[73] Assignees: Institut Pasteur, Paris, France; Medical Research Council, London, United Kingdom; Assistance Publique; Universite Paris VI, both of Paris, France

[21] Appl. No.: 929,206

[22] Filed: Aug. 14, 1992

Related U.S. Application Data

[63] Continuation-in-part of Ser. No. 875,940, Apr. 30, 1992, abandoned.
[51] Int. Cl.⁶ .................. C12Q 1/68; C07H 21/04
[52] U.S. Cl. .................. 435/6; 435/810; 436/501; 436/63; 536/22.1; 536/23.1; 536/24.31; 536/24.32; 536/24.33; 935/77; 935/78
[58] Field of Search .................. 435/6, 91.1, 810; 436/501, 63; 536/22.1, 23.1, 24.31–24.33; 935/77, 78, 88; 514/2, 44

[56] References Cited

U.S. PATENT DOCUMENTS 4,683,195  7/1987  Mullis et al. .................. 435/6

OTHER PUBLICATIONS

Zhang et al. (1992) Nature, vol. 358, pp. 591–593.

*Primary Examiner*—W. Gary Jones
*Assistant Examiner*—Ardin H. Marschel
*Attorney, Agent, or Firm*—Finnegan, Henderson, Farabow, Garrett & Dunner

[57] ABSTRACT

Multi-drug resistant strains of *Mycobacterium tuberculosis* represent a considerable threat to public health worldwide. Resistance to isoniazid (INH), a key component of anti-tuberculosis regimens, is often associated with loss of catalase activity and virulence. The katG gene, encoding HPI catalase-peroxidase, mediates INH-sensitivity and that the high level resistance encountered clinically may be due to deletions, insertions or point mutations which reduce or eliminate the expression of the catalase gene in the chromosomal region encompassing katG. INH-resistant strains of *Mycobacterium tuberculosis* are detected by nucleic acid hybridization with a unique nucleic acid sequence or by amplification techniques.

22 Claims, 7 Drawing Sheets

| Strains/plasmids | restriction map | MIC INH | Catalase |
|---|---|---|---|
| M.smegmatis MC²155 | | 32 | 0.123 |
| BH1 | | 512 | 0.055 |
| BH1/pBH4 | | 8 | 0.283 |
| pYZ55 | | 8 | nd |
| pBAK-EK +/− | | 512/512 | nd |
| pBAK-KE +/− | | 8/512 | nd |
| pBAK-KB +/− | | 512/512 | nd |

| | |
|---|---|
| *M. tuberculosis* | APLNSWPDNASLDKARRLLWPSKKKYGKKLSWADLIV |
| *E. coli* | **********V***********I*Q***Q*I*****FI |
| *B. stearothermophilus* | **********N*******C*GR**RNT*T*-*LGPICS |

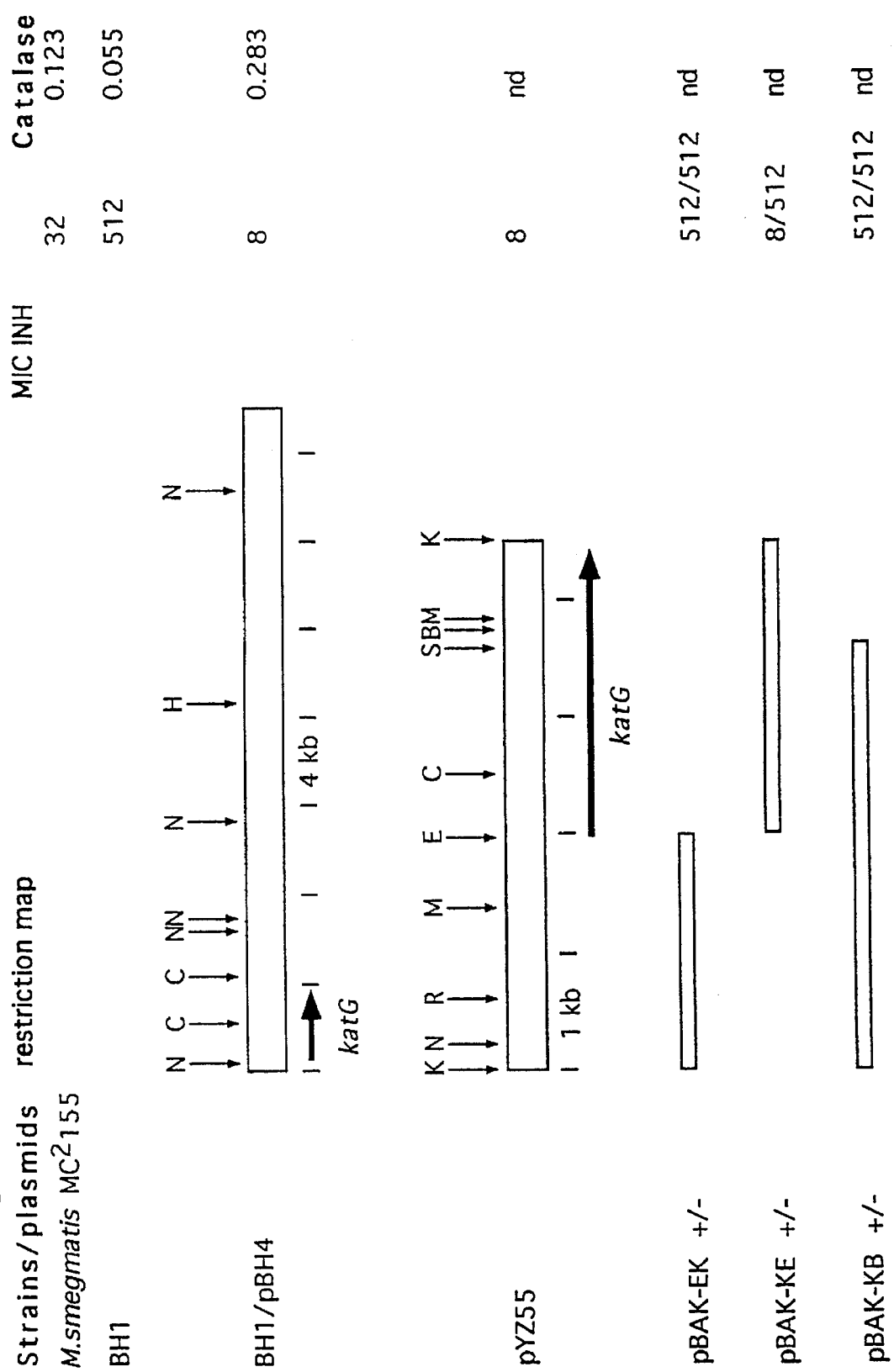

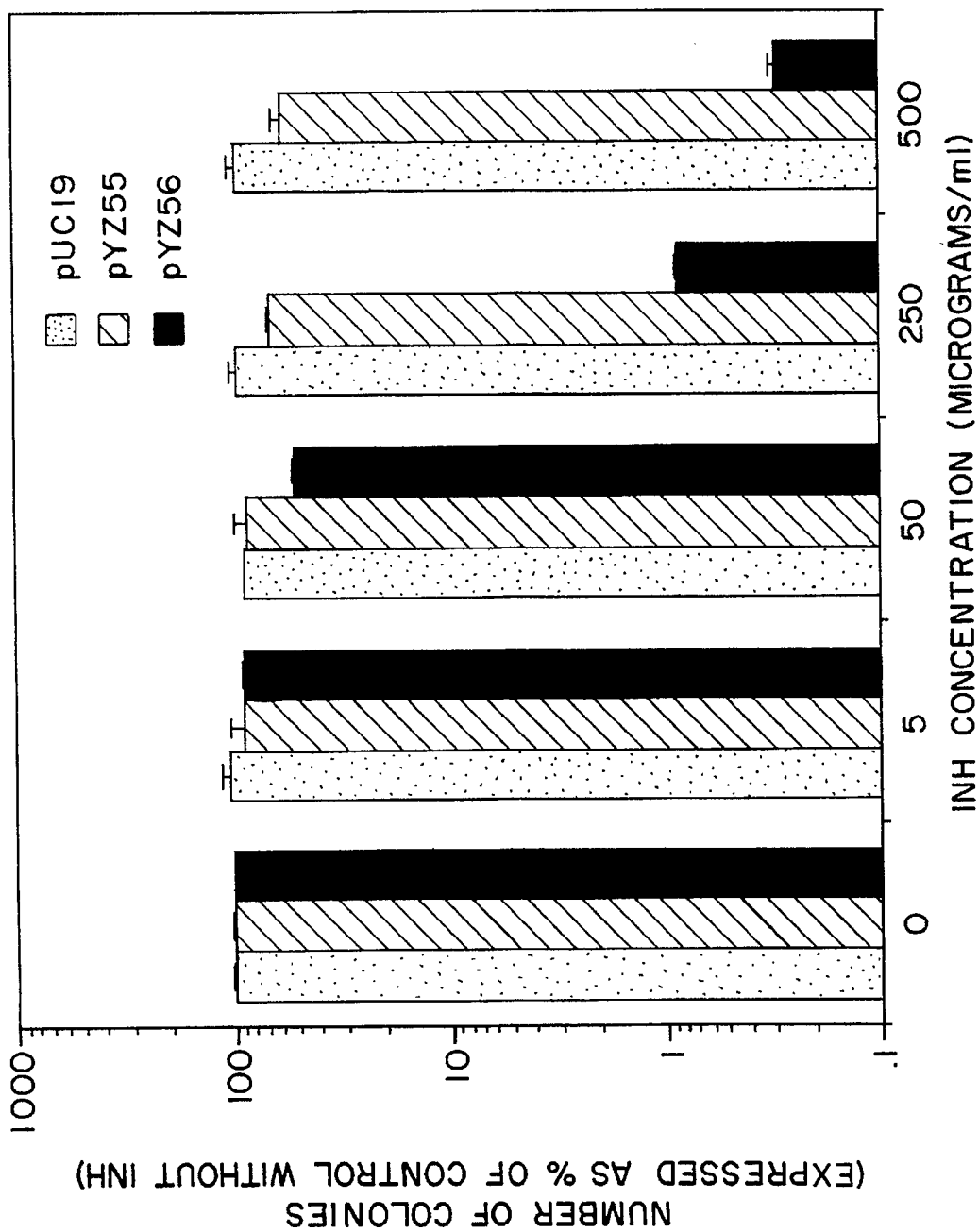

SEQUENCE LISTING ( 1 ) GENERAL INFORMATION:

( i i i ) NUMBER OF SEQUENCES: 8

( 2 ) INFORMATION FOR SEQ ID NO:1:

( i ) SEQUENCE CHARACTERISTICS:
        ( A ) LENGTH: 39 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:1:

TTCATCCGCA TGGCCTGGCA CGGCGCGGGC ACCTACGC     39

( 2 ) INFORMATION FOR SEQ ID NO:2:

( i ) SEQUENCE CHARACTERISTICS:
        ( A ) LENGTH: 120 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:2:

```
Met Thr Met Ile Thr Pro Ser Leu His Ala Cys Arg Ser Thr Leu Glu
 1           5                  10                  15

Asp Pro His Pro Thr Leu Arg Asp His Ile Arg Asp His Ser Pro Ile
            20                  25                  30

Thr Pro Thr Pro Gly Arg Asn Ala Met Pro Glu Gln His Pro Pro Ile
            35                  40                  45

Thr Glu Thr Thr Thr Gly Ala Ala Ser Asn Gly Cys Pro Val Val Gly
    50                  55                  60

His Met Lys Tyr Pro Val Glu Gly Gly Gly Asn Gln Asp Trp Trp Pro
65                  70                  75                  80

Asn Arg Leu Asn Leu Lys Val Leu His Gln Asn Pro Ala Val Ala Asp
            85                  90                  95

Pro Met Gly Ala Ala Phe Asp Tyr Ala Ala Glu Val Ala Thr Ser Arg
            100                 105                 110
```

```
        Leu Asp Ala Leu Thr Arg Asp Ile
                115                 120
```

( 2 ) INFORMATION FOR SEQ ID NO:3:

( i ) SEQUENCE CHARACTERISTICS:
    ( A ) LENGTH: 360 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:3:

```
ATGACCATGA TTACGCCAAG CTTGCATGCC TGCAGGTCGA CTCTAGAGGA TCCCCATCCG      60
ACACTTCGCG ATCACATCCG TGATCACAGC CCGATAACAC CAACTCCTGG AAGGAATGCT    120
GTGCCCGAGC AACACCCACC CATTACAGAA ACCACCACCG GAGCCGCTAG CAACGGCTGT    180
CCCGTCGTGG GTCATATGAA ATACCCCGTC GAGGGCGGCG GAAACCAGGA CTGGTGGCCC    240
AACCGGCTCA ATCTGAAGGT ACTGCACCAA AACCCGGCCG TCGCTGACCC GATGGGTGCG    300
GCGTTCGACT ATGCCGCGGA GGTCGCGACC AGTCGACTTG ACGCCCTGAC GCGGGACATC    360
```

( 2 ) INFORMATION FOR SEQ ID NO:4:

( i ) SEQUENCE CHARACTERISTICS:
    ( A ) LENGTH: 78 amino acids
    ( B ) TYPE: amino acid
    ( D ) TOPOLOGY: linear ( i i ) MOLECULE TYPE: peptide ( x i ) SEQUENCE DESCRIPTION: SEQ ID NO:4:

```
Met Ser Thr Ser Asp Asp Ile His Asn Thr Thr Ala Thr Gly Lys Cys
1               5                   10                  15

Pro Phe His Gln Gly Gly His Asp Gln Ser Ala Gly Ala Gly Thr Thr
            20                  25                  30

Thr Arg Asp Trp Trp Pro Asn Gln Leu Arg Val Asp Leu Leu Asn Gln
        35                  40                  45

His Ser Asn Arg Ser Asn Pro Leu Gly Glu Asp Phe Asp Tyr Arg Lys
    50                  55                  60

Glu Phe Ser Lys Leu Asp Tyr Tyr Gly Leu Lys Lys Asp Leu
65                  70                  75
```

( 2 ) INFORMATION FOR SEQ ID NO:5:

( i ) SEQUENCE CHARACTERISTICS:
    ( A ) LENGTH: 37 amino acids
    ( B ) TYPE: amino acid
    ( D ) TOPOLOGY: linear ( i i ) MOLECULE TYPE: peptide ( x i ) SEQUENCE DESCRIPTION: SEQ ID NO:5:

```
Ala Pro Leu Asn Ser Trp Pro Asp Asn Ala Ser Leu Asp Lys Ala Arg
1               5                   10                  15

Arg Leu Leu Trp Pro Ser Lys Lys Lys Tyr Gly Lys Lys Leu Ser Trp
            20                  25                  30

Ala Asp Leu Ile Val
            35
```

( 2 ) INFORMATION FOR SEQ ID NO:6:

( i ) SEQUENCE CHARACTERISTICS:

(A) LENGTH: 37 amino acids
(B) TYPE: amino acid
(D) TOPOLOGY: linear (ii) MOLECULE TYPE: peptide (xi) SEQUENCE DESCRIPTION: SEQ ID NO:6:

| Ala | Pro | Leu | Asn | Ser | Trp | Pro | Asp | Asn | Val | Ser | Leu | Asp | Lys | Ala | Arg |
|---|---|---|---|---|---|---|---|---|---|---|---|---|---|---|---|
| 1 | | | | 5 | | | | | 10 | | | | | 15 | |

| Arg | Leu | Leu | Trp | Pro | Ile | Lys | Gln | Lys | Tyr | Gly | Gln | Lys | Ile | Ser | Trp |
|---|---|---|---|---|---|---|---|---|---|---|---|---|---|---|---|
| | | | 20 | | | | | 25 | | | | | 30 | | |

| Ala | Asp | Leu | Phe | Ile |
|---|---|---|---|---|
| | | 35 | | |

(2) INFORMATION FOR SEQ ID NO:7:

(i) SEQUENCE CHARACTERISTICS:
(A) LENGTH: 36 amino acids
(B) TYPE: amino acid
(D) TOPOLOGY: linear (ii) MOLECULE TYPE: peptide (xi) SEQUENCE DESCRIPTION: SEQ ID NO:7:

| Ala | Pro | Leu | Asn | Ser | Trp | Pro | Asp | Asn | Ala | Asn | Leu | Asp | Lys | Ala | Arg |
|---|---|---|---|---|---|---|---|---|---|---|---|---|---|---|---|
| 1 | | | | 5 | | | | | 10 | | | | | 15 | |

| Arg | Cys | Leu | Gly | Arg | Ser | Lys | Arg | Asn | Thr | Gly | Thr | Lys | Ser | Leu | Gly |
|---|---|---|---|---|---|---|---|---|---|---|---|---|---|---|---|
| | | | 20 | | | | | 25 | | | | | 30 | | |

| Pro | Ile | Cys | Ser |
|---|---|---|---|
| | | 35 | |

(2) INFORMATION FOR SEQ ID NO:8:

(i) SEQUENCE CHARACTERISTICS:
(A) LENGTH: 37 amino acids
(B) TYPE: amino acid
(D) TOPOLOGY: linear (ii) MOLECULE TYPE: peptide (xi) SEQUENCE DESCRIPTION: SEQ ID NO:8:

| Ala | Pro | Leu | Asn | Ser | Trp | Pro | Asp | Asn | Ala | Ser | Leu | Asp | Lys | Ala | Arg |
|---|---|---|---|---|---|---|---|---|---|---|---|---|---|---|---|
| 1 | | | | 5 | | | | | 10 | | | | | 15 | |

| Arg | Leu | Leu | Trp | Pro | Ser | Lys | Lys | Lys | Tyr | Gly | Lys | Lys | Leu | Ser | Trp |
|---|---|---|---|---|---|---|---|---|---|---|---|---|---|---|---|
| | | | 20 | | | | | 25 | | | | | 30 | | |

| Ala | Asp | Leu | Ile | Val |
|---|---|---|---|---|
| | | 35 | | |

RAPID DETECTION OF ISONIAZID RESISTANCE IN *MYCOBACTERIUM TUBERCULOSIS* PROBES FOR SELECTING NUCLEIC ACID ENCODING ISONIAZID RESISTANCE, AND METHODS AND KITS

This application is a continuation-in-part of application Ser. No. 875,940 filed on Apr. 30, 1992, now abandoned. This invention relates to the rapid detection of strains of *Mycobacterium tuberculosis* that are resistant to the antibiotic isoniazid. More particularly, this invention relates to a method of detecting isoniazid resistance in *Mycobacterium tuberculosis* by nucleic acid hybridization. This invention also relates to a nucleic acid probe and a kit for carrying out the nucleic acid hybridization.

BACKGROUND OF THE INVENTION

Despite more than a century of research since the discovery of *Mycobacterium tuberculosis*, the aetiological agent of tuberculosis, by Robert Koch, this disease remains one of the major causes of human morbidity and mortality. There are an estimated 3 million deaths annually attributable to tuberculosis (Snider 1989), and although the majority of these are in developing countries, the disease is assuming renewed importance in the West due to the increasing number of homeless people and the impact of the AIDS epidemic (Chaisson et al., 1987; Snider and Roper, 1992).

Isonicotinic acid hydrazide or isoniazid (INH) has been used in the treatment of tuberculosis for the last forty years due to its exquisite potency against the members of the "tuberculosis" groups—*Mycobacterium tuberculosis, M. bovis* and *M. africanum* (Middlebrook, 1952; Youatt, 1969). Neither the precise target of the drug, nor its mode of action are known and INH treatment results in the perturbation of several metabolic pathways. There is substantial evidence indicating that INH may act as an anti-metabolite of NAD and pyridoxal phosphate (Bekierkunst and Bricker, 1967; Sriprakash and Ramakrishnan, 1970; Winder and Collins, 1968, 1969, 1970), and other data indicating that the drug blocks the synthesis of the mycolic acids, which are responsible for the acid-fast character of mycobacterial cell walls (Winder and Collins 1970; Quemard et al., 1991). Shortly after its introduction, INH-resistant isolates of *Mycobacterium tuberculosis* emerged and, on characterization, were often found to have lost catalase-peroxidase activity and to show reduced virulence in guinea pigs (Middlebrook et al., 1954; Kubica et al., 1968; Sriprakash and Ramakrishnan, 1970).

Very recently, INH-resistance has acquired new significance owing to a tuberculosis epidemic in the USA due to multi-drug resistant (MDR) variants of *M. tuberculosis* (CDC, 1990; 1991a, b) and the demonstration that such strains were responsible for extensive nosocomial infections of HIV-infected individuals and health care workers (Snider and Roper, 1992). In view of the gravity of this problem, there exists a need in the art to determine the relationship between INH-resistance and catalase-peroxidase production.

More particularly, there is a need in the art to understand the molecular mechanisms involved in drug sensitivity. In addition, there is a need in the art to develop a simple test permitting the rapid identification of INH-resistant strains. Further, there is a need in the art for reagents to carry out such a test.

SUMMARY OF THE INVENTION

Accordingly, this invention aids in fulfilling these needs in the art by providing a process for detecting in vitro the presence of cells of a *Mycobacterium tuberculosis* resistant to isoniazid. The process comprises the steps of:

(A) depositing and fixing nucleic acids of the cells on a solid support, so as to make the nucleic acids accessible to a probe;

(B) contacting the fixed nucleic acids from step (A) with a probe under conditions permitting hybridization;

(C) washing the filter resulting from step (B), so as to eliminate any non-hybridized probe; and then (D) detecting any hybridized probe on the washed filter resulting from step (C).

The probe comprises a nucleic acid sequence which is present in a 2.5 kb EcoRV-KpnI fragment of plasmid pYZ55, wherein said fragment contains a BamHI cleavage site. This fragment has been found to be associated with intracellular DNA of isoniazid-sensitive *Mycobacterium tuberculosis* and is capable of distinguishing such antibiotic sensitive microorganisms from isoniazid-resistant *Mycobacterium tuberculosis*, which do not contain DNA that hybridizes with this fragment under the conditions described hereinafter.

This invention further provides nucleotide sequences, such as RNA and DNA, of isoniazid-resistant *Mycobacterium tuberculosis* encoding the region of the katG gene of *Mycobacterium tuberculosis* that imparts isoniazid sensitivity absent from isoniazid-resistant cells.

This invention also provides a probe consisting of a label, such as a radionuclide, bonded to a nucleotide sequence of the invention.

In addition, this invention provides a hybrid duplex molecule consisting essentially of a nucleotide sequence of the invention hydrogen bonded to a nucleotide sequence of complementary base sequence, such as DNA or RNA.

Also, this invention provides a process for selecting a nucleotide sequence coding for a catalase-peroxidase gene of *Mycobacterium tuberculosis*, or for a portion of such a nucleotide sequence, from a group of nucleotide sequences, which comprises the step of determining which of the nucleotide sequences hybridizes; to a nucleotide sequence of the invention. The nucleotide sequence can be a DNA sequence or an RNA sequence. The process can include the step of detecting a label on the nucleotide sequence.

Further, this invention provides a kit for the detection of *Mycobacterium tuberculosis* resistant to isoniazid. The kit comprises a container means containing a probe comprising a nucleic acid sequence, which is a 2.5 kb EcoRV-KpnI fragment of plasmid pYZ55, wherein the fragment contains a BamHI cleavage site. The kit also includes a container means containing a control preparation of nucleic acid.

The invention also covers compounds obtained as products of the action of the enzyme catalase, or a similar enzyme on isoniazid. The katG gene or a derivative of this gene which retains a similar activity can be used as a source of catalase protein. The new compounds are selected by reactivity on INH-resistant-mycobacterial strains by the antibiogram method such as described in H. David et al.'s "Methodes de laboratoire pour Mycobacteriologie clinique" edited by Pasteur Institute, ISBN N° 0995-2454.

BRIEF DESCRIPTION OF THE DRAWINGS

This invention will be described in greater detail by reference to the drawings in which:

FIG. 1 is a restriction map of an insert present in pYZ55 showing the location of katG.

FIG. 2 is a partial sequence of the M. tuberculosis catalase/peroxidase polypeptide and comparison with the HPI enzymes from E. coli and B. stearothermophilus. Identical residues are indicated by *.

FIG. 3 shows the detection of recombinant M. tuberculosis catalase/peroxidase by activity staining. Cell extracts were separated by polyacrylamide gel electrophoresis and stained for peroxidase (lanes 1-5) and catalase activity. Samples were from M. tuberculosis, lane 1; E. coli TG1, lanes 2, 6; TG1/pYZ55 (katG+), lanes 3 and 7; TG1/pBAK16 (lacZ'::katG), lanes 4 and 8; TG1/pYZ78 (=pYZ55 deleted fof 1.4 kb BamHI-KpnI fragment).

FIG. 4 shows the results of Southern blotting analysis of various M. tuberculosis strains using a 4.5 kb KpnI fragment as a probe. (A) Genomic DNA, digested with KpnI, was from strains H37Rv, lane 1; strain 12, lane 2; B1453, lane 3; strain 24, lane 4; 79112, lane 5; 12646, lane 6; 79665, lane 7. Strains B1453 and 24 are resistant to high levels of INH, strain 12 to low levels while the others are INH-sensitive. (B) As a control, the same blot was hybridized with a probe for the sodA gene (Zhang et al., 1991). Note the IS6110-mediated polymorphism associated with B1453.

FIG. 5. shows the INH-resistant M. smegmatis strain, BH1[11] (a derivative of strain mc$^2$-155[10]) was transformed with a pool of M. tuberculosis H37Rv shuttle cosmids (kindly provided by Dr. W. R. Jacobs, New York) and individual clones were scored for INH-susceptibility. Cosmid pBH4 consistently conferred drug susceptibility and the transformant overproduced catalase (assayed as in Heym). The restriction map of the DNA insert from pBH4 is shown along with that of the insert from pYZ55—a plasmid containing katG of M. tuberculosis H37Rv, isolated on the basis of hybridization with an oligonucleotide probe (5'-TTCATCCGCATGGCCTGGCACGGCGCGGGCACC TACCGC-3') SEQ ID No: 1 designed to match the amino acid sequence from a conserved region of E. coli HPI. Restriction sites for the following enzymes are indicated: B, BamH1; C, CaI; E, EcoRV; H, HindIII, K, KpnI; M, SmaI; N, NotI; R, EcoRI; S, SacI. Transformation of BH1 with a mycobacterial shuttle plasmid pBAK14[18] containing the 4.5 kb insert from pYZ55 similarly conferred INH-susceptibility. MIC's are also shown for BH1 transformed with subfragments derived from pYZ55 and inserted into pBAK14 in one (+) or other (-) orientation. The katG gene and the ability to confer INH-susceptibility both mapped to a 2.9 kb EcoRV-KpnI fragment (pBAK-KE+).

Figure 6C:
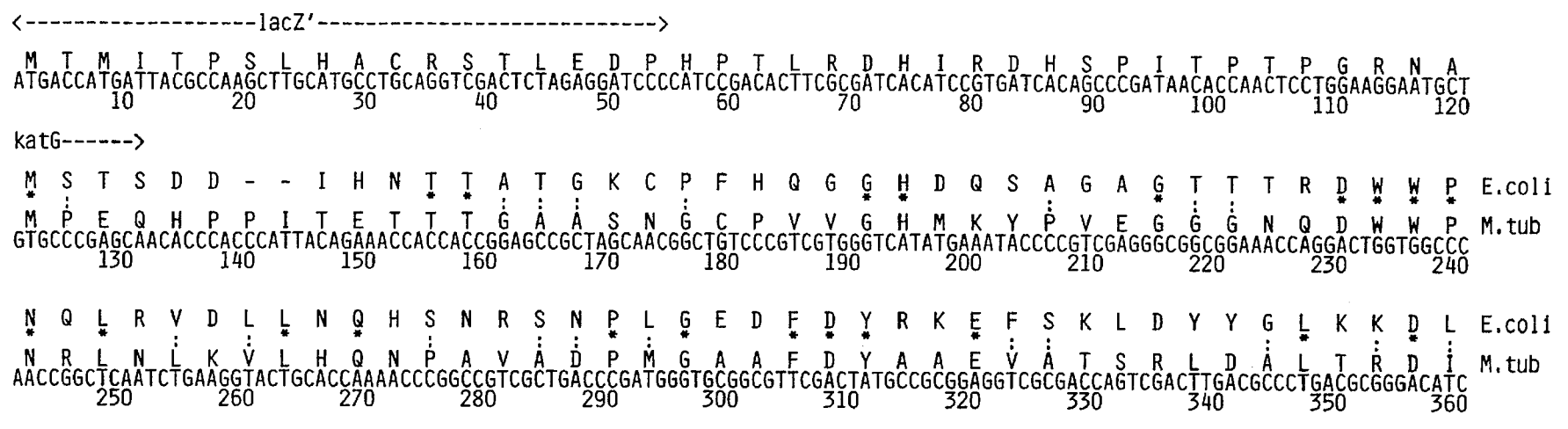

FIG. 6 shows extracts from M. tuberculosis H37Rv and from E. coli strains transformed with a variety of plasmid constructs that were prepared for activity gel analysis as described previously[18]. Non-denaturing gels containing 8% polyacrylamide were stained for catalase (panel A) and peroxidase (panel B) activities as described by Wayne and Diaz[19]. Lane 1, M. tuberculosis H37Rv; 2, E. coli UM2 (katE, katG, ref. 15); 3, E. coli UM2/pYZ55; 4, E. coli UM2/pYZ56 (the 2.9 kb EcoRV-KpnI fragment in pUC19, corresponding to pBAK-KE+ in FIG. 1); 5, E. coli UM2/pYZ57 (pYZ55 with a BamH1-KpnI deletion, corresponding to pBAK-KB+in FIG. 1). M. tuberculosis catalase and peroxidase activities migrated as two bands under these conditions (lane 1); the same pattern was seen for the recombinant enzyme expressed by pYZ55 (lane 3). pYZ56 (lane 4) expresses a protein of increased molecular weight due to a fusion between katG and lacZ' from the vector as shown in panel C. Panel C also shows partial sequence alignment with E. coli HPI (the complete sequence of the gene will be communicated elsewhere). In FIG. 6(c), the amino acid sequence for M. tuberculosis is identified by SEQ ID NO:2, the nucleotide sequence is identified by SEQ ID NO:3, and the amino acid sequence for E. coli is identified by SEQ ID NO:4.

FIG. 7 shows an E. coli strain with mutations in both katG and katE (UM2, ref. 15) that was transformed with pUC19 vector alone (hatched bars), pYZ55 expressing M. tuberculosis katG (open bars) and pYZ56 with high level expression of M. tuberculosis katG (solid bars). Overnight cultures in Luria-Bertani broth supplemented with appropriate antibiotics were plated out in the presence of varying concentrations of INH and colony forming units were assessed. Results of a representative experiment are shown with error bars indicating the standard deviation observed in triplicate samples. Overexpression of M. tuberculosis katG similarly conferred susceptibility to high concentrations of INH in E. coli UM255 (katG, katE, ref. 15), but had no effect on catalase-positive strains such as E. coli TG1. In some experiments, high concentrations of INH had detectable inhibitory effect on growth of UM2 and UM255, alone, but in all experiments inhibition of pYZ56-transformants was at least 10–100 fold greater than that observed in the corresponding vector controls.

FIG. 8 shows Southern blots prepared using genomic DNA from different M. tuberculosis strains, digested with KpnI, that were probed with (A) katG (the 4.5 kb KpnI fragment), and (B) the SOD gene (1.1 kb EcoR1-KpnI fragment, ref. 18). Labelling of probes and processing of blots was performed as described previously[16]. Lane 1, H37Rv; 2, strain 12—MIC 1.6 µg/mlINH; 3, B1453—MIC>50 µg/ml INH[20]; 4, strain 24—MIC>50 µg/ml INH; 5, 79112—INH-sensitive[21]; 6, 12646—INH-sensitive[21]; 7, 79665—INH-sensitive[21]. INH susceptibilities were confirmed by inoculation of Lowenstein-Jensen s opes containing differing concentrations of INH.

DETAILED DESCRIPTION OF PREFERRED EMBODIMENT

Figure 1:
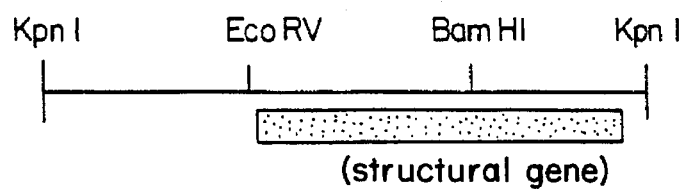
Figure 3:
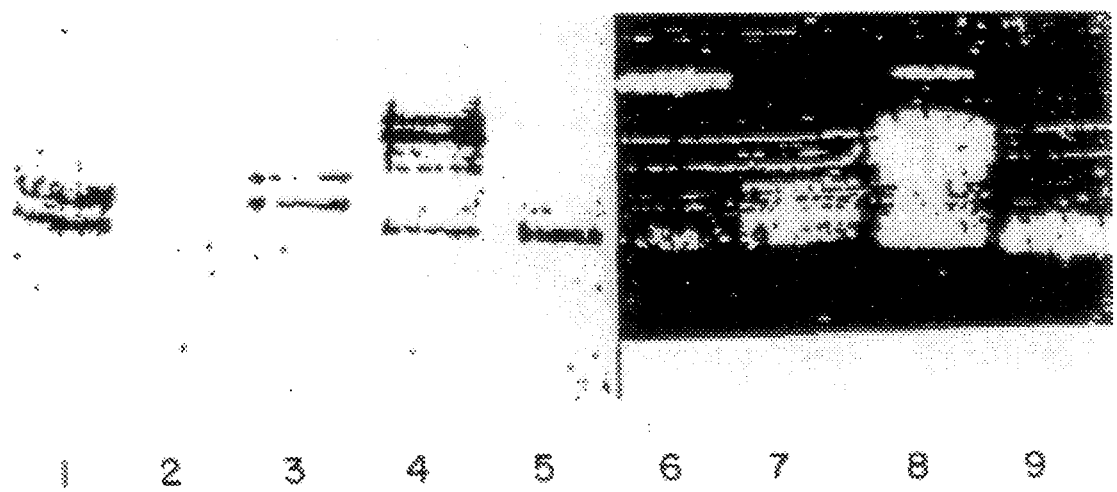
Figures 4A, 4B:
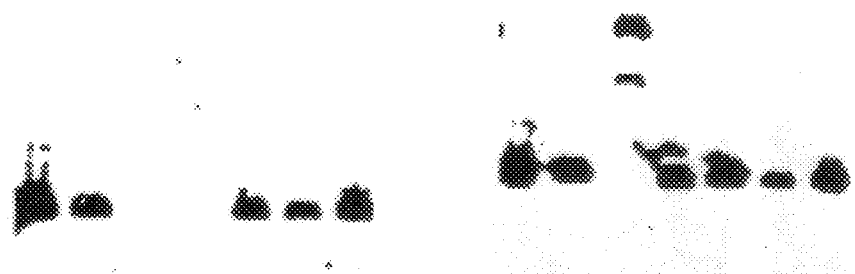
Figure 6A:
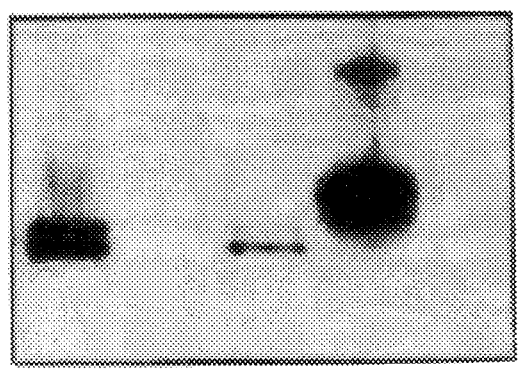
Figure 6B:
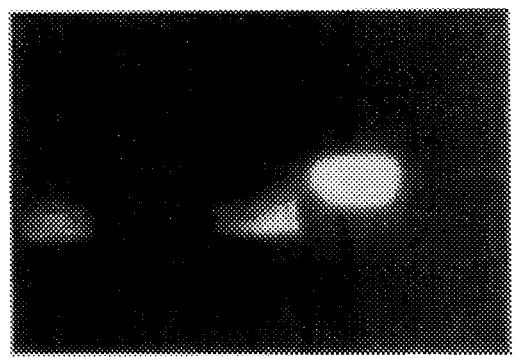
Figure 8A:
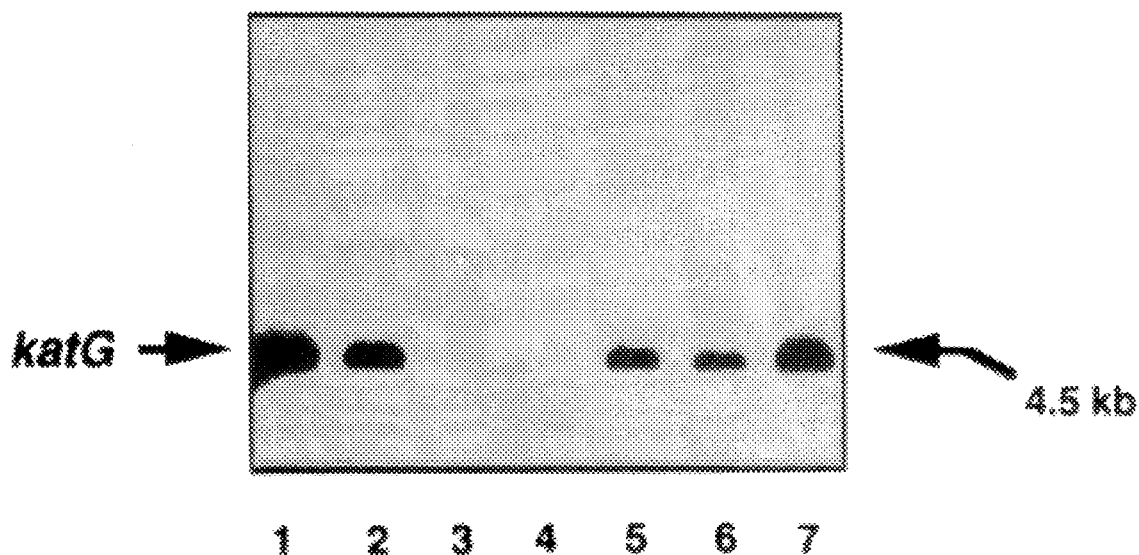
Figure 8B:
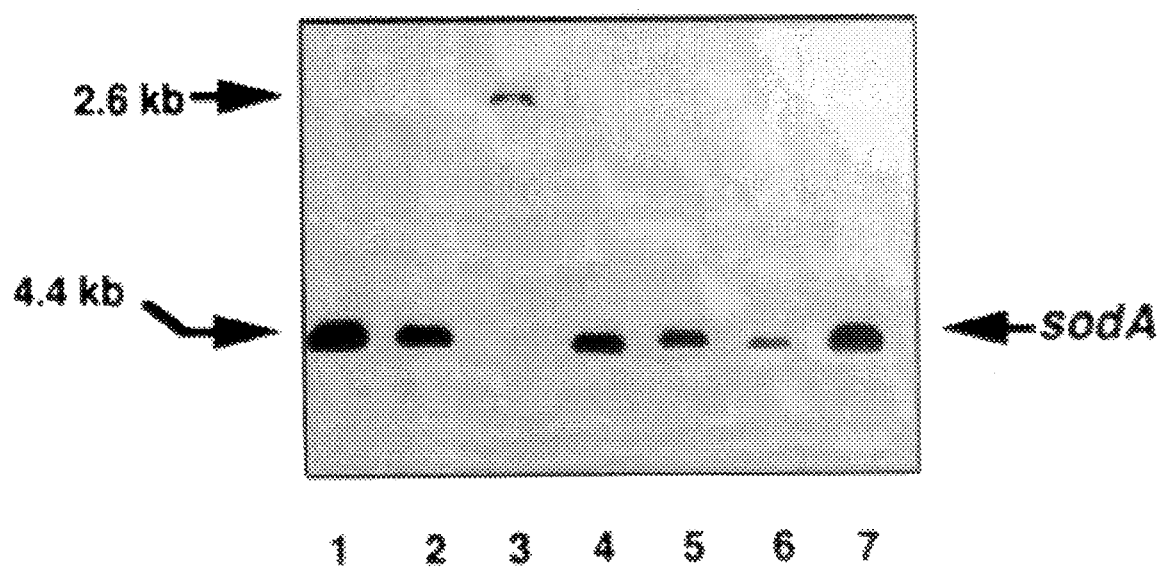

The recent emergence of large numbers of strains of M. tuberculosis showing multi-drug resistance in the United States is a most alarming development given the extreme contagiousness of this organism. This danger has been strikingly illustrated by several small tuberculosis epidemics in which a single patient infected with MDR M. tuberculosis has infected both HIV-positive individuals, prison guards and healthy nursing staff (CDC 1990, 1991; Daley et al., 1992; Snider and Roper, 1992). Given the gravity of the current worldwide HIV epidemic, it is conceivable that if AIDS patients in the West, like those in Africa, were to be infected with MDR M. tuberculosis strains (rather than members of the M. avium/M. intracellulare complex) widespread dissemination of the disease would result.

Isoniazid (INH) is a bactericidal drug which is particularly potent against the tuberculosis group of mycobacteria—Mycobacterium tuberculosis, M. bovis, and M. africanum—and, in consequence, it has been particularly effective in the treatment of tuberculosis. Standard anti-tuberculosis regimens generally include INH and rifampicin, often in combination with the weaker drugs, pyrazinamide, ethambutol or streptomycin. Besides its use in therapy INH is also given to close contacts of patients as a prophylactic measure.

INH-resistant mutants of M. tuberculosis, the agent of the human disease, show two levels of resistance: low (1 to 10 µg/ml) and high (10 to 100 µg/ml). INH-resistance is often associated with loss of catalase activity and virulence. Recently, owing to the AIDS epidemic, increased homelessness and declining social conditions, tuberculosis has re-emerged as a major public health problem in developed countries, particularly the USA. An alarming feature of the disease today is the emergence of multiple drug-resistant organisms and rapid nosocomial transmission to health care workers and HIV-infected patients. This has prompted CDC to propose new recommendations for the treatment of multiple resistant strains (at least INH and rifampicin) and the prevention of transmission. To obtain fresh insight into the problem of INH-resistance and to develop a rapid diagnostic test the following study was performed.

Clearly, it is essential to understand the mechanisms of resistance to INH and rifampicin, the main anti-tuberculosis agents, as this will allow novel chemotherapeutic strategies to be developed and facilitate the design of new compounds active against MDR strains.

This invention demonstrates that it is the catalase-peroxidase enzyme, HPI, which is the INH target, and it is suggested that this enzyme alone mediates toxicity. Compelling evidence of this conclusion was obtained by expression of the *M. tuberculosis* katG gene in a catalase-negative mutant of *E. coli* as this resulted in this bacterium becoming sensitive to INH. Moreover, the isolation of the *M. tuberculosis* INH-sensitivity gene, katG, is important as it will facilitate the rapid detection of INH-resistant strains by means of hybridization and PCR-based approaches. The high frequency of katG deletions in clinical strains, as shown here, should simplify this procedure.

Identification of an *M. tuberculosis* gene involved in INH-sensitivity

A heterologous approach was employed to isolate *M. tuberculosis* gene(s) involved in INH-sensitivity. BH1 is a spontaneous mutant of the easily transformable *M. smegmatis* strain $MC^2155$ (Snapper et al., 1990), that is resistant to 512 μg/ml of the INH and lacks catalase-peroxidase activity (Heym et al., 1992). As there is a strict correlation between INH-sensitivity and these enzyme activities, transformation of BH1 with a plasmid carrying the appropriate gene from *M. tuberculosis* should lead to their restoration and concomitant INH-sensitivity.

Consequently, DNA was prepared from a pool of *M. tuberculosis* shuttle cosmids in *Escherichia coli* and introduced into BH1 by electro-transformation. Over 1000 kanamycin-resistant transformants were then scored for INH-sensitivity, and four clones that failed to grow on medium containing 32 g/ml of INH, the MIC from wild type strain $MC^2155$, were obtained.

After re-transformation of BH1, only one of these, pBH4, consistently conferred the INH-sensitive phenotype. Restriction digests with BamHI, KpnI, NotI, ClaI and HindIII showed the *M. tuberculosis* chromosomal DNA carried by pBH4 to be about 30 kb in size.

When pBH4 was used as a hybridization probe to detect homologous clones in the library, a further eight shuttle cosmids were isolated. On transformation into BH1, five of these (T35, T646, T673, T79, T556) restored INH-sensitivity, and showed similar restriction profiles to pBH4 (data not shown). In particular, a KpnI fragment of 4.5 kb was present in all cases.

Attempts to subclone individual BamHI fragments did not give rise to transformants capable of complementing the lesion in BH1 suggesting that a BamHI site might be located in the gene of interest. In contrast, pBH5, a derivative of pBH4, was constructed by deletion of EcoRI fragments and this showed that a 7 kb segment was not required for restoration of INH-sensitivity.

Transformants harboring shuttle cosmids that complemented the INH-resistant mutation of BH1 were examined carefully and the MICs for several antibiotics were established. In all cases, the MIC for INH had been reduced from 512 to 8 μg/ml, a value lower than that of the sensitive strain $MC^2155$ (32 μg/ml). This hypersensitive phenotype suggested that the recombinant clones might be overproducing an enzyme capable of enhancing INH-toxicity. Enzymological studies showed that these transformants all produced about 2-fold more peroxidase and catalase than the wild type strain $MC^2155$, which is INH-sensitive (data not shown).

In addition to INH, many MDR-strains of *M. tuberculosis* are no longer sensitive to rifampicin, streptomycin, ethambutol and pyrazinamide. To examine the possibility that there might be a relationship between resistance to INH and these compounds, the MICs of several drugs for various *M. smegmatis* strains and their pBH4 transformants were determined, but no differences were found.

Cloning the *M. tuberculosis* catalase gene

A 45-mer oligonucleotide probe was designed based on the primary sequences of highly conserved regions in the catalase-peroxidase enzymes, HPI, of *E. coli* (Triggs-Raine et al., 1989), and *Bacillus stearothermophilus* (Loprasert et al., 1988). When genomic blots of *M. tuberculosis* DNA were probed with this oligonucleotide, specific bands were detected in most cases. As KpnI generated a unique fragment of 4.5 kb that hybridized strongly, this enzyme was used to produce a size selected library in pUC19.

Upon screening with the oligonucleotide probe, an appropriate clone, pYZ55, was obtained. A restriction map of the insert DNA illustrated that it corresponds exactly to part of pBH4. Independent confirmation was also obtained by cross-hybridization.

By means of various subcloning experiments the smallest fragment expressing *M. tuberculosis* catalase-peroxidase activity in *E. coli* was found to be a 2.5 kb EcoRV-KpnI fragment which, as expected, contained a cleavage site for BamHI. Partial DNA sequence analysis showed that the katG gene carried by pYZ55 encodes a catalase-peroxidase enzyme that is highly homologous to the HPI enzymes of *E. coli* and *B. stearothermophilus:*

| *M. tuberculosis* | APLNSWPDNASLDKARRLLWPSKKKYGKKLSWADLIV (SEQ ID NO: 5) |
|---|---|
| *E. coli* | ********V*********I*Q***Q*I*****FI (SEQ ID NO: 6) |
| *B. stearothermophilus* | ********N****C*GR**RNT*T*-*LGPICS (SEQ ID NO: 7) |

(FIG. 2; Triggs-Raine et al., 1988); (Loprasert et al., 1988). Identical residues are indicated by *. HPI activity was detected in both *E. coli* and *M. smegmatis* by staining (see below).

Catalase-peroxidase involvement in INH-sensitivity

Having cloned the *M. tuberculosis* katG gene, it was of immediate interest to investigate the genetic basis of the association between catalase-negativity and isoniazid resistance. A series of constructs was established in the shuttle vector pBAK and used to transform the INH-resistant *M. smegmatis* mutant BH1. Only those plasmids carrying a complete katG gene produced HPI and restored INH-sensitivity. The smallest of these, pBAK16, carried a 2.5 kb EcoRV-KpnI fragment thus demonstrating that the 2 kb region upstream of katG was not involved, and that catalase-peroxidase activity alone was sufficient to render mycobacteria susceptible to INH.

Cell-free extracts were separated by non-denaturating poly-acrylamide gel electrophoresis and stained for peroxidase and catalase activity. Under these conditions, the *M. tuberculosis* enzyme gave two bands of peroxidase activity (lane 1) which comigrated with catalase activity (data not shown; Heym et al., 1992).

When introduced into *E. coli* , the katG gene directed the synthesis of the same proteins, whereas pBAK16 produced proteins slightly larger in size. This is due to the construction of an in-frame lacZ::katG gene fusion. Activity stains were also performed with cell extracts of *M. smegmatis* . The presence of the katG gene from the *M. tuberculosis* in BH1 led to the production of catalase-peroxidase enzyme, which displayed the same electrophoretic mobility as the enzyme made in *M. tuberculosis*, or in *E. coli*, and the native HPI of *M. smegmatis*.

Basis of INH-resistance in *M. tuberculosis*

It has been known for many years that a subset of INH-resistant strains, particularly those resistant to the highest drug concentrations, are of lower virulence in the guinea pig and devoid of catalase activity. Genomic DNA was prepared from several clinical isolates of *M. tuberculosis* and analyzed by Southern blotting using the 4.5 kb KpnI fragment as a probe. In two highly resistant strains, B1453 and 24, the catalase gene has been deleted from the chromosome whereas in others (FIG. 3), such as strain 12, showing low level resistance it is still present but not expressed. Additional studies showed that the region immediately prior to katG was highly prone to rearrangements (data not shown).

*M. tuberculosis* HPI renders *E. coli* sensitive to INH

To determine whether the HPI enzyme of *M. tuberculosis* could confer INH sensitivity on *E. coli* , a series of catalase mutants was transformed with pBAK16 and the MICs determined. Wild type strains were not susceptible to INH, but mutants lacking both endogenous catalase activities, but harboring pBAK16, showed growth inhibition when high levels of INH (500 μg/ml) were present, whereas untransformed strains were insensitive.

For purposes of this invention, plasmid containing and the restriction endonuclease map shown in FIG. 5 was deposited in strain with the National Collection of Cultures of Microorganisms (C.N.C.M.) of the Institut Pasteur, in Paris, France on May 18, 1992, under culture collection accession No. I- 1209. This plasmid contains the nucleic acid sequence of the invention, namely, the 4.5 kb KpnI-KpnI fragment of plasmid pYZ55 having the BamHI cleavage site in the fragment.

In general, the invention features a method of detecting the presence of isoniazid-resistant *Mycobacterium tuberculosis* in a sample including providing at least one DNA or RNA probe capable of selectively hybridizing to isoniazid-sensitive *Mycobacterium tuberculosis* DNA to form detectable complexes. Detection is carried out with a sample under conditions which allow the probe to hybridize to isoniazid-sensitive *Mycobacterium tuberculosis* DNA present in the sample to form hybrid complexes and detecting the hybrid complexes as an indication of the presence of isoniazid-sensitive *Mycobacterium tuberculosis* in the sample. (The term "selectively hybridizing", as used herein, refers to a DNA or RNA probe which hybridizes only to isoniazid-sensitive *Mycobacterium tuberculosis* and not to isoniazid-sensitive *Mycobacterium tuberculosis*.) The sample can be comprised of the *Mycobacterium tuberculosis* cells or a portion of the cells or cell contents enriched in *Mycobacterium tuberculosis* nucleic acids, especially DNA. Hybridization can be carried out using conventional hybridization reagents. The particular hybridization conditions have not been found to be critical to the invention.

More particularly, DNA sequences from *Mycobacterium tuberculosis* can be analyzed by Southern blotting and hybridization. The techniques used for the present invention are described in Maniatis, Sambrook et al., (Cold Spring Harbor, Second Edition, 1989). DNA fragments can be separated on agarose gels and denatured in situ. The fragments can then be transferred from the gel to a water insoluble solid, porous support, such as a nitrocellulose filter, a nylon membrane, or an activated cellulose paper, where they are immobilized for example, the Hybond® membrane commercialized by Amersham are used. After prehybridization to reduce non-specific hybridization with the probe, the solid support is hybridized to the nucleic acid probe of the invention. The solid support is washed to remove unbound and weakly binding probe, and the resulting hybrid duplex molecule is examined. A convenient alternative approach is to hybridize oligonucleotides to the DNA denatured in the gel.

The amount of labeled probe which is present in the hybridization solution will vary widely, depending upon the nature of the label, the amount of the labeled probe which can reasonably bind to the filter, and the stringency of the hybridization. Generally, substantial excesses of the probe over stoichiometric will be employed to enhance the rate of binding of the probe to the fixed DNA.

Various degrees of stringency of hybridization can be employed. The more severe the conditions, the greater the complementarity that is required for hybridization between the probe and the polynucleotide for duplex formation. Severity can be controlled by temperature, probe concentration, probe length, ionic strength, time, and the like. Conveniently, the stringency of hybridization is varied by changing the polarity of the reactant solution. Temperatures to be employed can be empirically determined or determined from well known formulas developed for this purpose.

Unlike Southern hybridization where DNA fragments are transferred from an agarose gel to a solid support, the method of the invention can also be carried out by oligonucleotide hybridization in dried agarose gels. In this procedure, the agarose gel is dried and hybridization is carried out in situ using an oligonucleotide probe of the invention. This procedure is preferred where speed of detection and sensitivity may be desirable. The procedure can be carried out on agarose gels containing genomic or cloned DNA of *Mycobacterium tuberculosis.*

In addition, the method of this invention can be carried out by transfer of *Mycobacterium tuberculosis* DNA from polyacrylamide gels to nylon filters by electroblotting. Electroblotting may be desirable where time is of the essence, because electroblotting is typically faster than capillary blotting developed to transfer DNA from agarose gels. This method can be carried out in conjunction with UV-crosslinking. The polyacrylamide gel containing the samples to be tested is placed in contact with an appropriately prepared nylon filter. These are then sandwiched into an electroblotting apparatus and the DNA is transferred from the gel onto the filter using electric current. After a buffer rinse, the filter is ready to be prehybridized and hybridized or UV-crosslinked.

The method of the invention can be carried out using the nucleic acid probe of the invention for detecting *Mycobac-*

*terium tuberculosis* resistant to isoniazid. The probe can be detected using conventional techniques.

The nucleotides of the invention can be used as probes for the detection of a nucleotide sequence in a biological sample of *M. tuberculosis*. The polynucleotide probe can be labeled with an atom or inorganic radical, most commonly using a radionuclide, but also perhaps with a heavy metal. Radioactive labels include $^{32}$P, $^{3}$H, $^{14}$C, or the like. Any radioactive label can be employed, which provides for an adequate signal and has sufficient half-life. Other labels include ligands that can serve as a specific binding member to a labeled antibody, fluorescers, chemiluminscers, enzymes, antibodies which can serve as a specific binding pair member for a labeled ligand, and the like. The choice of the label will be governed by the effect of the label on the rate of hybridization and binding of the probe to the DNA RNA. It will be necessary that the label provide sufficient sensitivity to detect the amount of DNA or RNA available for hybridization.

In preferred embodiments of the invention, the probe is labeled with a radioactive isotope, e.g., $^{32}P$ or $^{125}I$, which can be incorporated into the probe, e.g., by nick-translation.

In other preferred embodiments, the probe is labeled with biotin, which reacts with avidin to which is bonded a chemical entity which, when the avidin is bonded to the biotin, renders the hybrid DNA complex capable of being detected, e.g., a fluorophore, which renders the hybrid DNA complex detectable fluormetrically; an electron-dense compound capable of rendering the hybrid DNA complexes detectable by an electron microscope; an antibody capable of rendering the hybrid DNA complexes immunologically detectable; or one of a catalyst/substrate pair capable of rendering the hybrid DNA complexes enzymatically detectable. Prior to contacting the bacteria with the probe, the *M. tuberculosis* bacteria can be lysed to release their DNA, which is then denatured and immobilized on an appropriate solid, DNA-binding support, such as a nitrocellulose membrane.

Another detection method, which does not require the labeling of the probe, is the so-called sandwich hybridization technique. In this assay, an unlabeled probe, contained in a single-stranded vector, hybridizes to isoniazid-sensitive *Mycobacterium tuberculosis* DNA, and a labeled, single-stranded vector, not containing the probe, hybridizes to the probe-containing vector, labeling the whole hybrid complex.

The sequences of the invention were derived by dideoxynucleotide sequencing. The base sequences of the nucleotides in are written in the 5'→3' direction. Each of the letters shown is a conventional designation for the following nucleotides:

| | |
|---|---|
| A | Adenine |
| G | Guanine |
| T | Thymine |
| C | Cytosine. |

The nucleotides of the invention can be prepared by the formation of 3'→5' phosphate linkages between nucleoside units using conventional chemical synthesis techniques. For example, the well-known phosphodiester, phosphotriester, and phosphite triester techniques, as well as known modifications of these approaches, can be employed. Deoxyribonucleotides can be prepared with automatic synthesis machines, such as those based on the phosphoramidite approach. Oligo- and polyribonucleotides can also be obtained with the aid of RNA ligase using conventional techniques.

The nucleotides of the invention are in a purified form. For instance, the nucleotides are free of human blood-derived proteins, human serum proteins, viral proteins, nucleotide sequences encoding these proteins, human tissue, and human tissue components. In addition, it is preferred that the nucleotides are free of other nucleic acids, extraneous proteins and lipids, and adventitious microorganisms, such as bacteria and viruses.

This invention of course includes variants of the nucleotide sequences of the invention or serotypic variants of the probes of the invention exhibiting the same selective hybridization properties as the probes identical herein.

The nucleotide sequences of the present invention can be employed in a DNA amplification process known as the polymerase chain reaction (PCR). See, e.g., S. Kwok et al., J. Virol., 61:1690–1694 (1987). PCR is advantageous because this technique is rapid.

DNA primer pairs of known sequence positioned 10–300 base pairs apart that are complementary to the plus and minus strands of the DNA to be amplified can be prepared by well known techniques for the synthesis of oligonucleotides. One end of each primer can be extended and modified to create restriction endonuclease sites when the primer is annealed to the PBMC DNA. The PCR reaction mixture can contain the PBMC DNA, the DNA primer pairs, four deoxyribonucleoside triphosphates, $MgCl_2$, DNA polymerase, and conventional buffers. The DNA can be amplified for a number of cycles. It is generally possible to increase the sensitivity of detection by using a multiplicity of cycles, each cycle consisting of a short period of denaturation of the PBMC DNA at an elevated temperature, cooling of the reaction mixture, and polymerization with the DNA polymerase.

Amplified sequences can be detected by the use of a technique termed oligomer restriction (OR). See, R. K. Saiki et al., Bio/Technology 3:1008–1012 (1985) and SSCP PNAS 1989, vol. 86, p. 2766–2770. For example, after amplification, a portion of the PCR reaction mixture can be separated and subjected to hybridization with an end-labeled nucleotide probe, such as a $^{32}p$ labelled adenosine triphosphate end-labeled probe. In OR, an end-labeled oligonucleotide probe hybridizes in solution to a region of the amplified sequence and, in the process, reconstitutes a specific endonuclease site. Thus, hybridization of the labeled probe with the amplified katG sequence yields a double-stranded DNA form that is sensitive to selective restriction enzyme digestion. After restriction with an endonuclease, the resulting samples can be analyzed on a polyacrylamide gel, and autoradiograms of the portion of the gel with the diagnostic labeled fragment can be obtained. The appearance of a diagnostic fragment (e.g., 10–15 bases in length) in the autoradiogram indicates the presence of katG sequences in the PBMCs.

Since it may be possible to increase the sensitivity of detection by using RNA instead of chromosomal DNA as the original template, this invention contemplates using RNA sequences that are complementary to the DNA sequences described herein. The RNA can be converted to complementary DNA with reverse transcriptase and then subjected to DNA amplification.

EXPERIMENTAL PROCEDURES

Bacterial strains and plasmids

Table 1 outlines the properties of the bacterial strains and plasmids used in this invention.

TABLE 1

Bacterial Strains And Plasmids

| Strains/plasmids | Characteristics |
|---|---|
| E. coli NM554 | |
| E. coli TG1 | supE hsd5 thi delta (lac-proAB) [traD36 proAB+lacI$^q$ lacZ delti M15] |
| E. coli UM2 | KatE |
| E. coli UM255 | KatE |
| M. tuberculosis H37Rv | Virulent strain originally isolated from tuberculosis patient |
| M. tuberculosis 12 | Clinical isolate resistant to low levels of INH (1–2 µg/ml) |
| M. tuberculosis B1453 | Clinical isolate resistant to high levels of INH (>50 µg/ml) |
| M. tuberculosis 24 | Clinical isolate resistant to high levels of INH (>50 µg/ml) |
| M. tuberculosis 79112 | Clinical isolate sensitive to INH |
| M. tuberculosis 12646 | Clinical isolate sensitive to INH |
| M. tuberculosis 79665 | Clinical isolate sensitive to INH |
| M. smegmatis MC$^2$155 | MC$^2$6 het |
| M. smegmatis BH1 | MC$^2$155 het katG |
| pBH4 | Shuttle cosmid, kat$^{G+}$, based on pYUB18 |
| pBH5 | Deleted version of pBH4, kat$^{G+}$, (7 kb-EcoRI) |
| pYZ55 | pUC19 derivative with 4.5 kb KpnI fragment, katG |
| pYZ78 | pUC19 derivative with 3.1 kb KpnI–BamHI fragment, katG– |
| pBAK14 | Mycobacterial shuttle vector |
| pBAK15 | Mycobacterial shuttle vector carrying 4.5 kb KpnI fragment (kat$^{G+}$) |
| pBAK16 | Mycobacterial shuttle vector carrying 2.5 kb EcoRV-KpnI fragment (kat$^+$) |

The *M. tuberculosis* H37 RV genomic library was constructed in the shuttle cosmid pYUB18 (Snapper et al., 1988) and kindly supplied by Dr. W. R. Jacobs. Other shuttle vectors employed were pYUB12 (Snapper et al., 1988) and pBAK14 (Zhang et al., 1991).

Microbiological techniques and enzymology

Details of antibiotics used, growth conditions, enzymology and MIC determinations can be found in Heym et al., (1992).

Nucleic acid techniques

Standard protocols were used for subcloning, Southern blotting, DNA sequencing, oligonucleotide biosynthesis, etc. (Maniatis et al., 1989; Eiglmeier et al., 1991).

Activity staining

The preparation of cell-free extracts of *E. coli* and mycobacteria has been described recently (Heym et al., 1992; Zhang et al., 1991). Native protein samples were separated by polyacrylamide gel electrophoresis as described by Laemmli (1970) except that SDS was omitted from all buffers, samples were not boiled and betamercaptoethanol was not included in the sample buffer. After electrophoresis of 50–100 µg protein samples on 7.5% polyacrylamide gels, catalase activity was detected by soaking the gel in 3mM H$_2$O$_2$ for 20 minutes with gentle shaking. An equal volume of 2% ferric chloride and 2% potassium ferricyanide was added and clear bands of catalase activity revealed by illumination with light. Peroxidase activity was detected as brown bands after soaking gels in a solution containing 0.2–0.5 mg/ml diaminobenzidine and 1.5 mM H$_2$O$_2$ for 30–120 minutes.

To generate a highly toxic compound it seems most likely that the *M. tuberculosis* HPI enzyme peroxidatively activates INH (Youatt, 1969; Gayathri-Devi et al., 1975). Now that the katG gene has been isolated and characterized, it should be possible to make new derivatives of INH, which can be activated in a similar manner.

REFERENCES CITED IN SPECIFICATION

Bekierkunst, A. & Bricker, A. (1967). Studies on the mode of action of isoniazid on mycobacteria. *Arch. Biochem. Biophys.* 122:385–392.

C.D.C. Outbreak of multidrug-resistant tuberculosis—Texas, California, and Pennsylvania. MMWR 1990(b), 39:369–372.

C.D.C. Nosocomial transmission of multidrug-resistant tuberculosis among HIV-infected persons—Florida and New York 1988–1991. MMWR 1991(a) 40:585–591.

C.D.C. Transmission of multidrug-resistant tuberculosis from an HIV-positive client in a residential substance abuse treatment facility. Michigan. MMWR 1991(b), 40:129–131.

Chaisson, R. E., Schecter, G. F., Theuer, C. P., Rutherford, G. W., Echenberg, D. F., Hopewell, P. C. (1987). Tuberculosis in patients with the acquired immunodeficiency syndrome. *Am. Rev. Respir. Dis.,* 23:56–74.

Daley, C. L., Small, P. M., Schecter, G. F., Schoolnik, G. K., McAdam, R. A., Jacobs, W. R., and Hopewell, P. C. (1992). An outbreak of tuberculosis with accelerated progression among persons infected with the human immunodeficiency virus. An analysis using restriction-fragment-length-polymorphism. *N. Engl. J. Med.,* 326:231–235.

Eiglmeier, K., Honore, N., and Cole, S. T. (1991). Towards the integration of foreign DNA into the chromosome of *Mycobacterium leprae. Research in Microbiology,* 142:617–622.

Gayathri Devi, B., Shaila, M. S., Ramakrishnan, T., and Gopinathan, K. P. (1975). The purification and properties of peroxidase in *Mycobacterium tuberculosis* H37RV and its possible role in the mechanism of action of isonicotinic acid hydrazide. *Biochem. J.,* 149:187–197.

Heym, B. and Cole, S. T. (1992). Isolation and characterization of isoniazid-resistant mutants of *Mycobacterium smegmatis* and *M. aurum. Res. Microbiol.,* submitted.

Kubica, G. P., Jones Jr., W. D., Abbott, V. D., Beam, R. E., Kilburn, J. O., and Cater Jr., J. C. (1966). Differential identification of mycobacteria. I. Tests on catalase activity. *Am. Rev. Resp. Dis.,* 94:400–405.

Laemmli, U.K., (1970). Cleavage of structural proteins during the assembly of the head of bacteriophage-T4. *Nature* (London) 227:680–685.

Loprasert, S., Negoro, S., and Okada, H. (1989). Cloning, nucleotide sequence, and expression in *Escherichia coli* of the *Bacillus stearotherrrmophilus* peroxidase gene (perA). *J. Bacteriol.,* 171:4871–4875.

Maniatis, T., Sambrook, J., and Fritsch, E. F. (1989). Molecular cloning. A laboratory manual. Second Edition 1989. Cold Spring Harbor Laboratory Press.

Middlebrook, G. (1954). Isoniazid-resistance and catalase activity of tubercle bacilli. *Am. Rev. Tuberc.,* 69:471–472.

Middlebrook, G., Cohn, M. L., and Schaefer, W. B. (1954). Studies on isoniazid and tubercle bacilli. III. The isolation, drug-susceptibility, and catalase-testing of tubercle bacilli from isoniazid-treated patients. *Am. Rev. Tuberc.,* 70:852–872.

Quemard, A., Lacave, C., and Laneelle, G. (1991). Isoniazid inhibition of mycolic acid synthesis by cell extracts of sensitive and resistant strains of *Mycobacterium aurum. Antimicrob. Ag. Chem.,* 35:1035–1039.

Snapper, S. B., Lugosi, L., Jekkel, A., Melton, R. E., Kieser, T., Bloom, B. R., and Jacobs, W. R. (1988). Lysogeny and transformation in mycobacteria: stable expression of foreign genes. *Proc. Natl. Acad. Sci. USA*, 85:6987–6991.

Snapper, S. B., Melton, R. E., Mustafa, S., Kieser, T., and Jacobs, W. R. (1990). Isolation and characterization of efficient plasmid transformation mutants of *Mycobacterium smegmatis*. *Mol. Microbiol.*, 4:1911–1919.

Snider, D. (1989). *Rev. Inf. Dis.*, 335.

Snider Jr., D. E. and Roper, W. L. (1992). The new tuberculosis. *The New England Journal of Medicine*, 326:703–705.

Sriprakash, K. S. and Ramakrishnan, T. (1970). Isoniazid-resistant mutants of *Mycobacterium tuberculosis* H37Rv: Uptake of isoniazid and the properties of NADase inhibitor. *J. Gen. Microbiol.*, 60:125–132.

Triggs-Raine, B. L., Doble, B. W., Mulvey, M. R., Sorby, P.A., and Loewen, P.C. (1988). Nucleotide sequence of kagG, encoding catalase HPI of *Escherichia coli*. *J. Bacteriol.*, 170:4415–4419.

Winder, F. and Collins, P. (1968). The effect of isoniazid on nicotinamide nucleotide levels in *Mycobacterium bovis*, strain BCG. *Amer. Rev. Respir. Dis.*, 97:719–720.

Winder, F. and Collins, P. (1969). The effect of isoniazid on nicotinamide nucleotide concentrations in tubercle bacilli. *Amer. Rev. Respir. Dis.*, 100:101–103.

Winder, F. and Collins, P. (1968). Inhibition by isoniazid of synthesis of mycolic acids in *Mycobacterium tuberculosis*, *J. Gen. Microbiol.*, 63:41–48.

Youatt, J. (1969). A review of the action of isoniazid. *Am. Rev. Respir. Dis.*, 99:729–749.

Zhang, Y., Lathigra, R., Garbe, T., Catty, D., and Young, D. (1991) Genetic analysis of superoxide dismutase, the 23 kilodalton antigen of *Mycobacterium tuberculosis*. *Mol. Microbiol.*, 5:381–391.

---

What is claimed is:

1. A process for detecting in vitro the presence of nucleic acids of a *Mycobacterium tuberculosis* which is resistant to isoniazid, wherein the process comprises the steps of:
   (A) depositing and fixing nucleic acids of *Mycobacterium tuberculosis* on a solid support, so as to make the nucleic acids accessible to a probe;
   (B) contacting said fixed nucleic acids from step (A) with the probe under conditions permitting selective hybridization;

(C) washing said solid support resulting from step (B), so as to eliminate any non-hybridized probe; and then (D) detecting any hybridized probe on said washed solid support resulting from step (C) as an indication of the presence of nucleic acids of a *Mycobacterium tuberculosis* which is resistant to isoniazid;

wherein said probe comprises a nucleic acid, which is 2.5 kb EcoRV-KpnI fragment of plasmid pYZ55, and wherein said fragment contains a BamHI cleavage site.

2. A process as claimed in claim 1 wherein the probe has a label selected from the group consisting of radioactive, enzymatic, fluorescent, and luminescent labels.

3. A process for detecting in vitro the presence of cells of a *Mycobacterium tuberculosis* which is resistant to isoniazid, wherein the process comprises the steps of:

(A) depositing and fixing nucleic acids of the cells on a solid support, so as to make the nucleic acids accessible to a probe;

(B) contacting said fixed nucleic acids from step (A) with a probe under conditions permitting selective hybridization;

(C) washing said solid support resulting from step (B), so as to eliminate any non-hybridized probe; and then (D) detecting any hybridized probe on said washed solid support resulting from step (C) as an indication of the presence of nucleic acids of a *Mycobacterium tuberculosis* which is resistant to isoniazid;

wherein said probe comprises a nucleic acid which encodes a polypeptide of the formula APLNSWPDNASLDKAR-RLLWPSKKKYGKKLSWADLIV (SEQ ID NO:8).

4. A process as claimed in claim 3, wherein the probe has a label selected from the group consisting of radioactive, enzymatic, fluorescent, and luminescent labels.

5. A method of detecting the presence of *Mycobacterium tuberculosis* which is resistant to isoniazid in a bacteria-containing sample comprising (A) providing a sample suspected of containing *Mycobacterium tuberculosis* which is resistant to isoniazid;

(B) lysing the bacteria in said sample to release their DNA;

(C) denaturing said released DNA;

(D) providing a probe, which is capable of stably hybridizing to DNA from *Mycobacterium tuberculosis* species which are resistant to isoniazid, wherein said probe comprises a 2.5 kb EcoRV-KpnI fragment of plasmid pYZ55, wherein said fragment contains a BamHI cleavage site;

(E) contacting said DNA probe with said released DNA in said sample under conditions which allow said probe to selectively hybridize to DNA from *Mycobacterium tuberculosis* which is resistant to isoniazid, if present in said sample, to form hybrid DNA complexes; and (F) detecting said hybrid DNA complexes as an indication of the presence in said sample of *Mycobacterium tubercuriosis* which is resistant to isoniazid.

6. The method of claim 5, wherein said probe is labeled.

7. The method of claim 6, wherein said label is either capable of being detected or is capable of selectively bonding to an indicator to form a detectable complex.

8. The method of claim 7, wherein said probe is labeled with a radioactive isotope.

9. The method of claim 7, wherein said label is a non-isotopic marker and said indicator is avidin to which is bonded a chemical entity which, when said avidin is bonded to said marker on said hybrid DNA complex, is capable of being detected.

10. The method of claim 9, wherein said chemical entity is a fluorophore, which renders said hybrid DNA complexes fluorometrically detectable.

11. The method of claim 9, wherein said chemical entity is an electron-dense compound, which renders said hybrid DNA complexes detectable by an electron microscope.

12. The method of claim 9, wherein said chemical entity is an antibody, which renders said hybrid DNA complexes immunologically detectable.

13. The method of claim 9, wherein said chemical entity is one of a catalyst/substrate pair, which renders said hybrid DNA complexes enzymatically detectable.

14. The method of claim 5, wherein prior to contacting said DNA with said probe, said bacteria are separated from said sample and said DNA is immobilized on a DNA binding support.

15. The method of claim 14, wherein said support is a nitro-cellulose membrane.

16. A kit for the detection of *Mycobacterium tuberculosis* which is resistant to isoniazid, wherein the kit comprises:

(A) a container means containing a probe comprising a nucleic acid, which is a 2.5 kb EcoRV-KpnI fragment of plasmid pYZ55, wherein said fragment contains a BamHI cleavage site; and (B) a container means containing a control preparation of nucleic acid.

17. A kit as claimed in claim 16, wherein the probe has a label selected from the group consisting of radioactive, enzymatic, fluorescent, and luminescent labels.

18. A nucleic acid probe for detecting *Mycobacterium tuberculosis* which is resistant to isoniazid, wherein said probe consists of a 2.5 kb EcoRV-KpnI fragment of plasmid pYZ55, wherein said fragment contains a BamHI cleavage site.

19. The probe as claimed in claim 18, which is DNA free of human serum proteins, viral proteins, bacterial proteins, and nucleic acid encoding said proteins.

20. The probe as claimed in claim 18, which is free of human tissue.

21. The probe as claimed in claim 18 having radionuclide label bonded to the probe.

22. The method of claim 9 wherein the label is biotin and the indicator is avidin.

\* \* \* \* \*